United States Patent [19]

Presta et al.

[11] 4,396,285
[45] Aug. 2, 1983

[54] LASER SYSTEM AND ITS METHOD OF USE

[75] Inventors: Peter S. Presta, Menlo Park; Charles R. Munnerlyn, Sunnyvale; John A. Gibson, San Jose, all of Calif.

[73] Assignee: Coherent, Inc., Palo Alto, Calif.

[21] Appl. No.: 180,549

[22] Filed: Aug. 25, 1980

[51] Int. Cl.³ .................. A61B 17/36; G01B 11/27; G02B 5/10

[52] U.S. Cl. ................ 356/138; 128/303.1; 350/296

[58] Field of Search .................. 356/138, 153; 128/303.1, 395; 350/293, 296; 219/121 LU, 121 LV, 121 LW, 121 L

[56] References Cited

U.S. PATENT DOCUMENTS

| | | | |
|---|---|---|---|
| 2,252,246 | 8/1941 | Bergmans et al. | 350/443 |
| 3,353,893 | 11/1967 | Bamberger et al. | 350/302 |
| 3,456,651 | 7/1969 | Smart | 356/138 |
| 3,514,776 | 5/1970 | Mulready | 343/6 |
| 3,669,522 | 6/1972 | Anderson | 350/6 |
| 3,796,220 | 3/1974 | Bredeneier | 128/303.1 |
| 3,865,114 | 2/1975 | Sharon | 128/303.1 |
| 3,986,767 | 10/1976 | Rexer et al. | 350/299 |
| 4,030,816 | 6/1977 | Belke et al. | 350/294 |
| 4,072,147 | 2/1978 | Hett | 128/6 |
| 4,141,362 | 2/1979 | Wurster | 128/303.1 |
| 4,211,229 | 7/1980 | Wurster | 128/303.1 |

FOREIGN PATENT DOCUMENTS

| | | | |
|---|---|---|---|
| 55-59033 | 5/1980 | Japan | 350/296 |
| 790069 | 2/1958 | United Kingdom | 350/293 |

OTHER PUBLICATIONS

Meyer et al., "A Laser Stimulator for the Study of Cutaneous Thermal & Pain Sensations", *IEEE Trans. on Bio Med. Eng.*, vol. BME-23, 1-1976, pp. 54-60.

*Primary Examiner*—William H. Punter
*Attorney, Agent, or Firm*—Limbach, Limbach & Sutton

[57] ABSTRACT

A laser system for medical applications has at least two lasers and a movable concave reflector. The lasers are capable of generating beams of coherent electromagnetic radiation. One of the beams, an aiming beam, is aligned to impinge the reflector, to reflect therefrom and to impinge a biological specimen. The reflector is moved until the beam is aligned to impinge the desired position. The reflector is held stationary and the second beam is generated. The second beam is also aligned to impinge the reflector to reflect therefrom and to impinge the same desired position as that impinged by the first beam.

10 Claims, 4 Drawing Figures

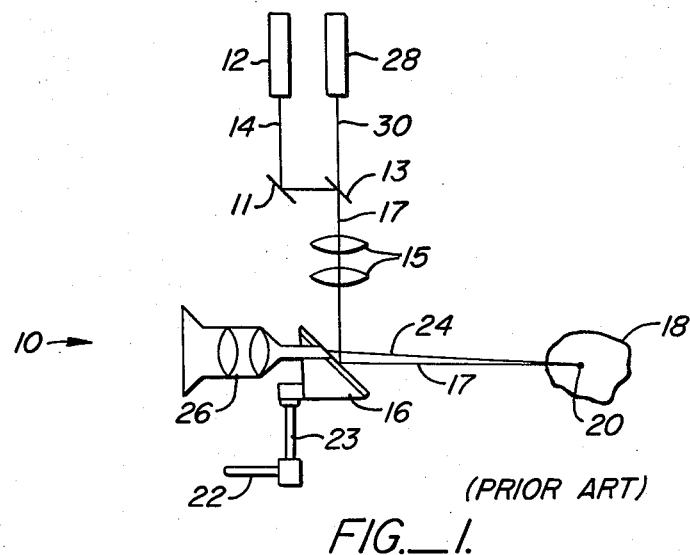
FIG._1. (PRIOR ART)
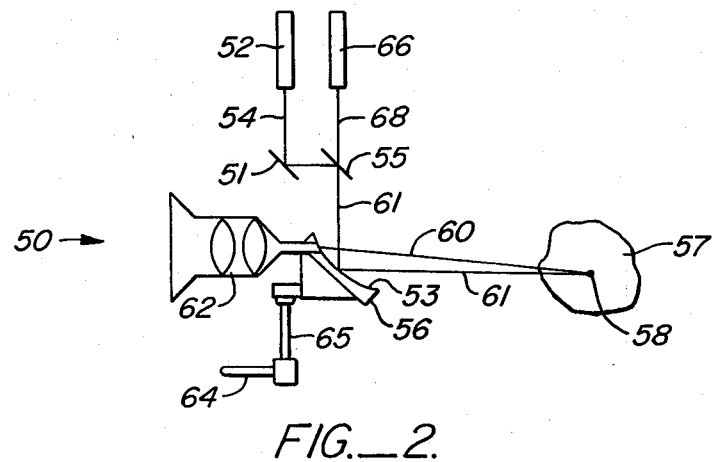
FIG._2.
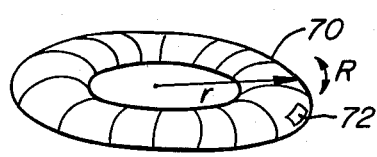
FIG._3a.
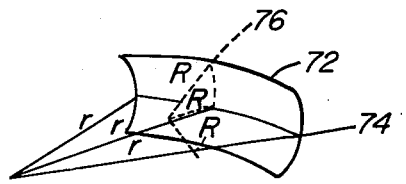
FIG._3b.

LASER SYSTEM AND ITS METHOD OF USE

BACKGROUND OF THE INVENTION

The present invention relates to a laser system and its method of use, and more particularly, to a laser system having two or more laser beams and a concave reflector for use for example in medical applications.

Lasers, and laser systems for use in medical applications are well known. A typical application is the use of laser for microsurgery. In such application, a laser system is attached to an operating microscope. The system comprises two coaxial beams: A first tracking beam, usually at 632 nm. wavelength and is used for aiming the beam to the desired spot on the biological specimen; and an infrared beam, usually at 10.6 microns wavelength for treatment. The laser beams are directed on a path perpendicular to the microscope's field of vision. A flat mirror is typically placed directly before the microscope and is set at 45 degrees with respect to the laser beams. The beams reflected from the flat mirror would then be coaxial with respect to the visual axis of the microscope.

Because the microscope must be adapted for work at several different distances, the laser system must be adapted as well. Heretofore, lenses such as zinc selenide (ZnSe) are used, either singularly or in pairs, to focus the beams of light. The use of the focusing lenses, however, results in several problems. First, power loss in system results from the absorptive property of the material used in the lens. Secondly, because of chromatic aberration, beams impinging the lenses at slightly off axis will not have a common focal point. Finally, the lenses are expensive to manufacture and the material zinc selenide is quite toxic.

SUMMARY OF THE INVENTION

In accordance with the apparatus of the present invention, a laser system for directing coherent electromagnetic radiation to a desired location on a biological specimen has two laser beams. The beams are aligned to impinge a movable concave reflector and to reflect therefrom to impinge a biological specimen. The reflector is capable of being positioned with respect to the first and second laser beams and cooperating with the two beams to cause the two beams to impinge the biological specimen at the same location.

The present invention also provides a method for using the foregoing apparatus.

BRIEF DESCRIPTION OF THE DRAWINGS

FIG. 1 is a schematic side view of an apparatus of the prior art.

FIG. 2 is a schematic side view of the apparatus of the present invention.

FIG. 3a is a perspective view of a toroidally shaped object.

FIG. 3b is an enlargement of a section of FIG. 3a.

DETAILED DESCRIPTION OF THE INVENTION

Referring to FIG. 1, there is shown a laser system 10 of the prior art. The system 10 comprises a first laser 12 capable of generating first beam 14. First beam 14 is aligned to impinge a mirror 11. The mirror 11 is placed at 45 degrees with respect to the path of the first beam 14. The first beam 14 reflected from the mirror 11 impinges a splitter 13. Reflecting from the splitter 13, the first beam 14 traverses along the path 17. The first beam 14 is then focused by a pair of zinc selenide (ZnSe) lens 15 onto a flat reflector 16. The first beam 14 is reflected from the reflector 16, travels along the path 17 and impinges the spot 20 on the biological specimen 18.

Reflector 16 is capable of being moved by a joy stick 22 with linkage 23 to the reflector 16. In general, the reflector 16 may be moved in two different directions. When the reflector 16 is moved by the joy stick 22, the first beam 14 reflected from the reflector 16 impinges a different portion of the specimen 18. Thus, by appropriately moving the reflector 16, the first beam 14 may be guided to impinge the desired location 20 on the specimen 18.

The reflector 16 is placed at approximately 45 degrees with respect to the path 17. Thus, the first beam 14 reflected from the reflector 16 traversing the path 17 is perpendicular to the beam incident to the reflector 16. When the first beam 14 is on the desired spot 20, the image is seen along the visual axis 24 by a user, typically a surgeon thru the microscope 26, which magnifies the image. The visual axis 24 is approximately parallel to the portion of path 17 reflected from the reflector 16. At that point, a second laser 28 is activated, generating a second beam 30 of radiation. The second beam 30 passes thru the splitter 13 and also traverses along the path 17, the path previously traversed by the first beam 14. The second beam 30 also passes through the lenses 15 to impinge the reflector 16. The reflector 16 is positioned with respect to first laser 12 and the second laser 28 such that without further movement of the reflector 16, the second beam 30 reflected from the reflector 16 also impinges the same location 20 of the biological specimen 18, as previously impinged by the first beam 14. The second beam 30 is used to treat the specimen 18 at the location 20. Examples of such application include microsurgery and photo coagulation. Typically, the first beam 14, called an aiming beam, is the output from a helium-neon (He-Ne) laser. This is operating at a wavelength of 632 nm. The second laser 28 is typically a $CO_2$ laser and generates a second beam 30 having a wavelength of 10.6 microns.

Referring to FIG. 2, there is shown the laser system 50 of the present invention. The laser system 50 is identical to the laser system 10 of FIG. 1 with the exception of the removal of the lens 15 and replacement of the flat reflector 16 by a concave reflector 56. The reflector 56 has a concave reflective surface 53. One specific configuration for the reflector 56 is of a reflector 56 whose reflective surface 53 is in a shape of a section of a toroid. This will be described in detail hereinafter. The laser system 50 comprises a first laser 52 capable of generating a first beam 54. The first beam 54 is aligned to impinge a mirror 51 and a splitter 55, all of which are similar to that previously described. The first beam 54 then traverses along the path 61 to impinge the concave reflector 56 on the concave reflective surface 53 and to be reflected therefrom to impinge the biological specimen 57. Typically, the concave reflector 56 is placed at about 45 degrees with respect to the first beam 54 from the first laser 52. In other words, the incident portion of the first beam 54 incident to the reflector 56 is substantially perpendicular to the reflected portion of the first beam 54 reflected from the reflector 56.

A microscope 62 is directed along a visual axis 60 which is substantially coaxially aligned with the reflected portion of the path 61 reflected from the reflector 56. The microscope 62 magnifies the image as seen along the visual axis 60. The image is of the portion of the specimen 57 upon which the first beam 54 has impinged. The concave reflector 56 is capable of being moved by a joy stick 64 which is connected to the reflector 56 by the linkage 65.

By moving the reflector 56, the reflected portion of the first beam 54 reflected from the reflector 56 would impinge different portions of the specimen 57. Thus, the reflector 56 may be used to move the reflected portion of the first beam 54 to impinge the desired location 58 of the specimen 57. When this is achieved, the image, magnified by the microscope 62, is seen by the user who then activates the second laser 66. The second laser 66 generates a second beam 68 of radiation which is also directed at the reflective surface 53 of the concave reflector 56 along path 61 through the splitter 55. The second beam 68 reflected from the reflector 56 also impinges the specimen 57, at the same location 58 as previously impinged by the first beam 54 from the first laser 52. The second beam 68 impinges the same location 58 of the specimen 56 without further movement of the reflector 56.

In one example of use, the first laser 52 is a helium-neon laser and as described hereinabove, produces a wavelength at 632 nm. The first beam 54 has negligible effect upon the specimen 57 at the desired location 58. When this first beam 54 has been aimed at the desired location, the second laser 66, typically a $CO_2$ laser, generates a second beam 68 at the wavelength of 10.6 microns. The photons from the second beam 68 cause a thermal reaction at the desired location 58 of the specimen 57. A typical thermal reaction may be microsurgery of the desired location 58.

In another example of use, the first laser 52 and the second laser 66 are replaced by a single laser. The first beam 54 and the second beam 68 are different power intensities of the same beam. Specifically, an Argon laser operating at 588 nm. is used. The first beam 54 is an attenuated (weaker) beam used for aiming the beam to the desired location. When this is accomplished the attenuator is removed, which then becomes the second beam 66 and which is applied. An example of use is photocoagulation.

The use of mirror 51 and splitter 55 to cause the first and second beams 54 and 68 respectively to traverse the same path 61, is to increase the accuracy of alignment.

In the method of the present invention, a first beam 54 of coherent electromagnetic radiation is generated by a first laser 52. The first beam 54 is directed to a movable reflector 56 having a concave reflective surface 53. First beam 54 is reflected from concave reflective surface 53 of the reflector 56 and impinges the biological specimen 57. The reflector 56 is moved until the first beam 54 impinges the specimen 57 at the desired location 58. Thereafter, a second beam 68 of coherent electromagnetic radiation is produced by a second laser 66. The second beam 68 is directed to impinge the concave reflective surface 53 of the reflector 56. The reflector 56 is held stationary. Second beam 68 reflected from the reflector 56 impinges the specimen 57 at the same desired location 58 as that previously impinged by the first beam 54, causing a thermal reaction between the second beam 66 and the specimen 57 at the location 58.

Referring to FIG. 3a, there is shown a perspective view of a toroidally shaped object 70. The toroid 70 may be thought of as analogous in shape to an inner tube. A section 72 of the toroid 70 has the desired shape for the reflective surface 53 of reflector 56 of FIG. 2. The section 72 is shown in greater detail in FIG. 3b. In general, a toroidal section 72 has two radii; a major one and a minor one. The major radius 74 is shown as having a radius of r; whereas a minor radius 76 is shown as having a radius of R. The plane of the major radius 74 is perpendicular to the plane of the mirror radius 76. The use of a reflective surface 53 shaped in a section of a toroid in the apparatus of the present invention is the discovery that over small areas, the sectional toroidal surface may be used as approximation for parabolic surface or elliptical surface. The sectional toroidal surface, similar to the other aforementioned surfaces, causes the incident beam to be focused at a focal point. Where a sectional toroidal surface may be used in place of a parabolic surface or an elliptical surface, it is preferred because of ease of manufacture.

For a sectional toroidally shaped reflector 56 inclined at an angle approximately 45 degrees with respect to the first and second beams 54 and 68 respectively, astigmatism may result. Astigmatism is the result of rays in the plane of the tilt and rays in the plane perpendicular to the tilt not being in focus at the same distance from the surface of the reflector 56. To eliminate astigmatism for light reflecting through 90 degrees as that shown in FIG. 2, using a reflecting toroidal reflector 56, it has been found through Coddington's equations that the tangential curvature must be twice the sagittal curvature. Thus, r must be equal to twice R. Of course, the relationship between r and R would change for light reflecting through other angles.

It can be seen that by replacing the lens and mirror system of the prior art by a concave reflector of the present invention a number of improvements result. First, because focusing is accomplished with a single reflector, instead of at least one lens and one reflector, power transmission losses are minimized. Then too, the elimination of the lenses result in fewer mechanical mounts and cost savings result from eliminating the use of the costly lens. Finally, chromatic aberration is totally eliminated and alignment and focusing accuracies are increased.

What is claimed is:

1. A beam delivery system for directing a first and a second beam of coherent electromagnetic radiation of different frequencies to a desired location on a biological specimen, said system comprising:
   means for generating said first and second beams of coherent electromagnetic radiation;
   a movable reflector having a substantially toroidally shaped reflective surface;
   said first beam aligned to impinge said reflector on said surface and to reflect therefrom to impinge said biological specimen;
   means for moving said reflector in two axes to focus the first beam at said desired location; and
   said second beam being aligned to impinge said reflector on said surface, to reflect therefrom and focus at the same desired location, without further movement of said reflector.

2. The system of claim 1 further comprising means for magnifying the image of said location.

3. The system of claim 1 wherein said first beam has negligible effect on said specimen at said location.

4. The system of claim 3 wherein said second beam causes a thermal reaction of said specimen at said location.

5. The system of claim 4 wherein said first beam is at a wavelength of 632 nm and said second beam is at a wavelength of 10.6 microns.

6. The system of claim 1 or 3 wherein said reflective surface is shaped in a section of a toroid.

7. A method of applying coherent electromagnetic radiation to a desired location on a biological specimen, said method comprising:

generating a first beam of coherent electromagnetic radiation;

directing said first beam to a movable reflector having a substantially toroidally shaped reflective surface;

reflecting said first beam from said reflective surface of said reflector;

impinging said biological specimen with said first beam reflected from said reflector;

moving said reflector in two axes until said beam impinges said specimen and is focused at the desired location;

producing a second beam of coherent electromagnetic radiation, said second beam at a frequency different from said first beam; and directing said second beam to impinge the surface of said reflector, to reflect therefrom, to impinge said specimen, said second beam and said first beam aligned to impinge said reflective surface and to be focussed at the same location on said specimen.

8. The method of claim 7 further comprising the step of thermally reacting said second beam with said specimen at said location.

9. An optical system for directing a first and a second beam of coherent electromagnetic radiation to a desired location on a target, said system comprising:

first means for generating a first beam of coherent radiation at a first wavelength;

second means for generating a second beam of coherent radiation at a second wavelength;

said first wavelength different from said second wavelength;

a movable reflector having a substantially toroidally shaped reflective surface;

said first beam aligned to impinge said reflector on said reflective surface and to reflect therefrom to impinge said target;

means for moving said reflector in two axes to focus the first beam at said desired location; and said second beam being aligned to impinge said reflector on said reflective surface, to reflect therefrom and focus at the same desired location, without further movement of said reflector.

10. The system of claim 9 wherein said reflective surface is shaped in a section of a toroid.

* * * * *